(12) United States Patent
Kane

(10) Patent No.: US 8,106,544 B2
(45) Date of Patent: Jan. 31, 2012

(54) ELECTRO-MAGNET BASED TELESCOPING ARTIFICIAL MUSCLE ACTUATOR

(76) Inventor: Seth Andrew Kane, Tenafly, NJ (US)

( * ) Notice: Subject to any disclaimer, the term of this patent is extended or adjusted under 35 U.S.C. 154(b) by 139 days.

(21) Appl. No.: 12/380,055

(22) Filed: Feb. 23, 2009

(65) Prior Publication Data

US 2010/0217404 A1 Aug. 26, 2010

(51) Int. Cl.
*H02K 41/02* (2006.01)
(52) U.S. Cl. .................... 310/12.01; 310/12.04
(58) Field of Classification Search ........... 310/12.04, 310/12.15, 12.01, 12.19
See application file for complete search history.

(56) References Cited

U.S. PATENT DOCUMENTS

| | | | |
|---|---|---|---|
| 4,703,297 A | 10/1987 | Nagasaka | |
| 6,223,648 B1 | 5/2001 | Erickson | |
| 6,380,832 B2 * | 4/2002 | Oyama et al. | 335/281 |
| 6,781,284 B1 | 8/2004 | Pelrine | |
| 6,960,847 B2 | 11/2005 | Suzuki | |
| 7,443,059 B2 * | 10/2008 | Kobayashi et al. | 310/12.04 |
| 7,474,018 B2 * | 1/2009 | Shimizu et al. | 310/12.22 |
| 2007/0186712 A1 | 8/2007 | Ferraresi | |
| 2007/0193267 A1 | 8/2007 | He | |

FOREIGN PATENT DOCUMENTS

WO 9727822 A1 8/1997

OTHER PUBLICATIONS

Anthony, Textbook of Anatomy and Physiology, 9th edition, 1975, C.Y. Mosby Company, USA. 108-120.
Gray, Anatomy of the Human Body, 22nd edition, 1930, Lea and Febiger, Philadelphia, PA, USA. 362-374.
Martini, Human Anatomy, 6th edition, 2009, Pearson Education, San Francisco, CA, USA.238-255.
Silverthorn, Human Physiology: An integrated approach, 4th edition, 2007, Pearson Cummings, San Francisco, CA, USA. 397-420.

* cited by examiner

*Primary Examiner* — Nguyen N Hanh

(57) ABSTRACT

The device described herein is an Electro-magnet based Telescoping Artificial Muscle Actuator. This device uses a centrally located electromagnet which acts on permanent magnets and ferrous components housed within telescoping sections of this device. This device is intended to be linked into chains with other identical devices, with those chains then linked into bundles. This arrangement allows devices of this type to simulate the action and control mechanisms of natural muscles. This device is intended for use in prosthetic, robotic, and implantable applications.

14 Claims, 2 Drawing Sheets

ELECTRO-MAGNET BASED TELESCOPING ARTIFICIAL MUSCLE ACTUATOR

CROSS REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

1. Field of the Invention

The field to which this invention pertains is to that of prosthetic and robotic motor systems and functional soft tissue biomechanical implants.

2. Description of Related Art

Current prosthetic devices employ rotary servos controlled by computer systems. These servos require computers to adapt signals coming from a body into appropriate control of rotary servos. These apparatuses require heavy batteries and do not provide the dexterity, or in most cases, the strength of a biological motor system. These drawbacks stem mostly from attempts to adapt robotic systems to biological ones, which are more robust, power efficient, and accurately controlled by the body. Current artificial muscle devices, meant to more effectively simulate the action of natural muscles, have been developed utilizing compressed air bladders and contractile polymers. These systems are still largely experimental and present significant drawbacks. Contractile polymer systems do not provide sufficient strength in current applications to replicate natural functioning. They also require computer control systems. Air bladder muscles, although strong and effective, still require computer control systems as well as power for air compressors. There are currently no technologies capable of being implanted in a living body to effectively replace a damaged or removed natural muscle.

BRIEF SUMMARY OF THE INVENTION

This invention, an Electro-magnet based Telescoping Artificial Muscle Actuator, is intended to address the drawbacks of the previous art in several ways. Firstly, this device is intended to be used in either prosthetic, robotic, or implant technologies. Secondly, this device is intended to be used with a control system that can directly convert biological control signals to comparable actuation control.

The actuator described herein is intended to be a modular component of a larger muscle system. This device is a simple spring loaded armature with a core electromagnet which powers contraction. This device is intended to be controlled primarily by an all or nothing control signal. Each control signal received by this device powers its activity directly. Each actuator is intended to be joined end to end to other identical actuators, with each addition providing additional power of contraction. These assemblies are intended to then be grouped with other similar chains of actuators. Control of such an apparatus would be affected through the number of chains of actuators being activated as well as the frequency of control signals received. This control system is akin to that of biological muscle and should be able to process signals directly from the body. This could be done using a direct nerve interface, conventional myoelectric detection, or myoelectric control systems in conjunction with nerve/muscle graft surgeries. Each action potential that would be sent to a natural muscle group would then activate the power supply of a specific actuator chain. The addition of signals from complimentary muscle groups would then activate additional actuator chains.

Power to this system would ideally be supplied through the use of high voltage capacitor banks linked to kinetic chargers; however, appropriate battery and stationary charger systems are acceptable. These actuators, in their chain and bundle arrangements, are intended to be used externally in prosthetic devices or in robotic applications. These actuators, in their chain and bundle arrangements, are intended to be used as biological implants if contained within an appropriate flexible biocompatible sheath with sections that allow for attachment to existing tendons and/or bones. The implantable application of this device should be used in conjunction with internal capacitor and control systems and external power storage and generation systems.

DETAILED DESCRIPTION OF THE INVENTION

Figure 1:
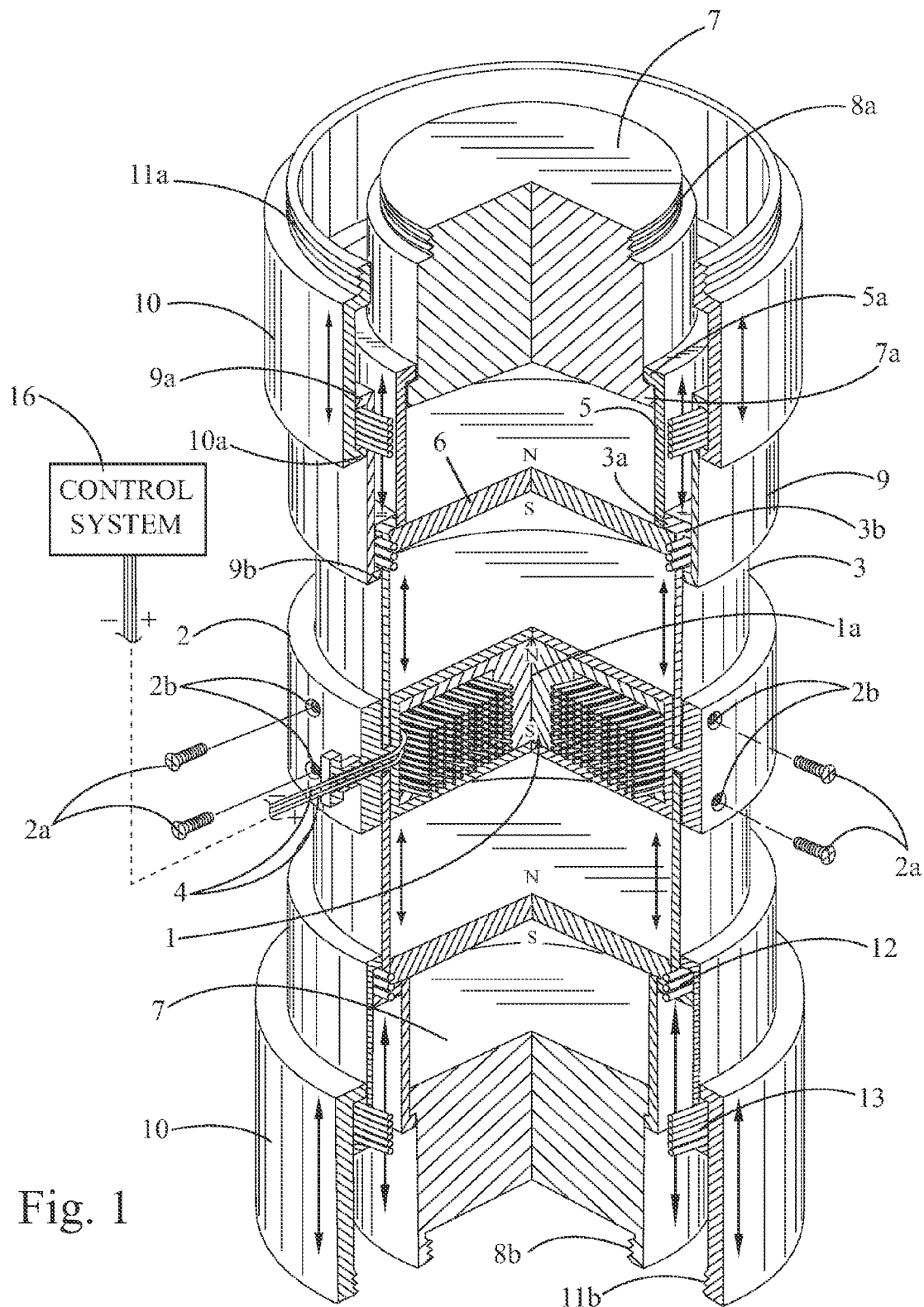
FIG. 1 is a perspective view of the devise with a cut section allowing the interior of the devise to be viewed.
Figure 2:
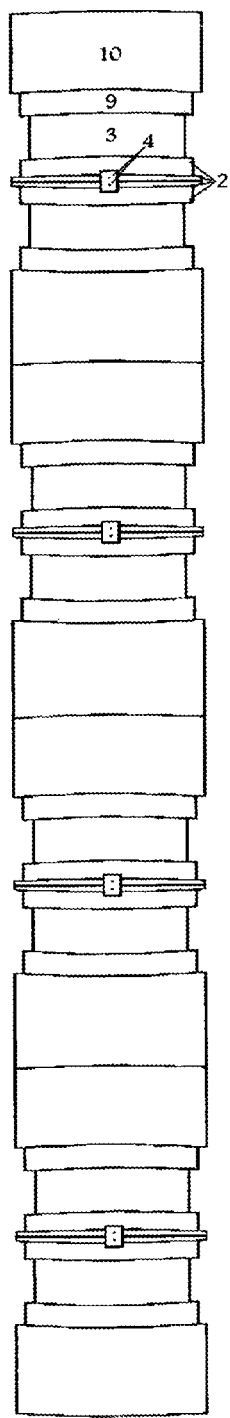
FIG. 2 is a view of the actuator chains grouped into a bundle.

The preferred embodiment of this device is as follows. The center of this device houses a solid ferrous core electromagnet (1). This electromagnet should have a solid core that is spindle shaped (1a). The electromagnet (1) should be housed in a nonferrous casing (2) that allows for attachment of two telescoping cylindrical parts (3). Each cylindrical telescoping part (3) should be mirrored around the central electromagnet (1) and be fitted into the electromagnet housing (2) by the use of screw threads or with screws (2a) with corresponding countersunk threaded holes (2b). Power leads (4) for the electromagnet (1) should pass through the electromagnet housing (2). All telescoping parts of this device (3), (5), and (9); except parts with threaded regions (7) and (10); occur in pairs mirrored around the central electromagnet (1). Threaded regions of telescoping parts (8a), (8b), (11a), and (11b) do not occur in mirrored pairs; one should have a male thread (8a) and (11a); and one a female thread (8b) and (11b) to allow for actuators to be connected end to end (FIG. 2).

The telescoping cylindrical parts (3) are open at one end with small lips (3a) protruding towards the center of the opening. These lips (3a) are meant to stop the motion of the telescoping cylindrical parts (5) by making contact with the permanent magnet bases (6) attached to the telescoping cylindrical parts (5). The telescoping cylindrical parts (3) must also have lips (3b) facing away from their openings to prevent motion of telescoping cylindrical parts (9). Telescoping cylindrical parts (5) are housed inside telescoping cylindrical parts (3).

Telescoping cylindrical parts (5) are comprised of nonferrous hollow cylinders with permanent magnets (6) attached to one side and with the other left open with a small lip (5a) protruding towards its center to contain telescoping cylindrical part (7). The polarity of the permanent magnets (6)

attached to each telescoping cylindrical part (5) should be oriented opposite to the polarity of the central electro magnet (1). The surfaces of the magnets (6) which face each other should have opposing polarities. Contained within telescoping cylindrical parts (5) are telescoping cylindrical parts (7). The telescoping cylindrical parts (7) are solid, ferrous, and have threaded ends (8a) or (8b) that extend beyond the open ends of telescoping cylindrical parts (5).

Telescoping cylindrical parts (7) have a lip at one end (7a) that contacts the lip (5a) of telescoping cylindrical parts (5). The telescoping cylindrical parts (7) are not identical mirrored pairs. One side of the pair of telescoping cylindrical parts (7) would have internal threads (8a) at the end protruding beyond the telescoping cylindrical parts (5), and the other would have external threads (8b) extending the same distance. This orientation, along with the threads (11a) or (11b), of telescoping cylindrical parts (10) allows actuators of this type to be joined together, end to end, into long chains (FIG. 2); to allow for increased force of contraction (to be discussed in detail below). Telescoping cylindrical parts (10) are nonferrous hollow cylinders which have one end that extends to the height of telescoping cylindrical parts (7). Each side of the pair of telescoping cylindrical parts (10) would have oppositely oriented threads (11a) or (11b) extending from the height of telescoping cylindrical parts (3), (5), and (9); and opposite ends with an internal lip (10a) that contacts telescoping cylindrical parts (9). Telescoping cylindrical parts (9) have a lip (9a) facing outward at its end closest to the threaded region of the device. Telescoping cylindrical parts (9) also have a lip (9b) facing the center of the device which contacts telescoping cylindrical parts (3). There is a spring (13) providing resistance in between telescoping cylindrical parts (10) and telescoping cylindrical parts (9). Telescoping cylindrical parts (9) are located inside telescoping cylindrical parts (10). Telescoping cylindrical parts (9) have a lip (9b) facing the center of the device which interacts with the outer lip (3b) telescoping cylindrical parts (3). There is another spring (12) located between telescoping cylindrical parts (9) and telescoping cylindrical parts (3).

The preferred dimensions of this device are that the central magnet (1) should have a sufficient number of coils to produce at least 0.5 to 1 lb of force. Dimensions of this device should be varied depending on the specific application for which it is used. This device must be capable of contracting to at least one half of its full extended length. This device must resist extension and tend to return to its contracted state if no internal or external forces are applied.

Each actuator of this type is intended to be joined end to end with other similar actuators, forming actuator chains (FIG. 2). Further bundling of these actuator chains (FIG. 3) is necessary to provide effective control of contraction strength and length. Increasing the amplitude of current supplied to this device will increase its contractile strength. Increasing the frequency of signals to this device accounts for an increase in duration and degree of contraction, with each signal control resulting in an all or nothing action of the actuator. Additional units to a chain of actuators and additions of actuator chains are intended to be the principle method of increasing the functional strength of contraction generated by this type of actuator.

Order of assembly of this device is as follows: telescoping cylindrical parts (7) are fitted into telescoping cylindrical parts (5), and then the magnets (6) are attached to telescoping cylindrical parts (5). Telescoping cylindrical parts (5) and attached magnets (6) with telescoping cylindrical parts (7) are then inserted into telescoping cylindrical parts (3). Springs (12) that provide resistance to the extension of the devise are then tilted around telescoping cylindrical parts (3). Then telescoping cylindrical parts (3), with spring (12) around it, and telescoping cylindrical parts (5) and (7) inside of it are fitted into telescoping cylindrical parts (9). Springs (13) that provides resistance to the extension of the devise are then placed around the outside of telescoping cylindrical parts (9). Telescoping cylindrical parts (9), with spring (13) around it; and telescoping cylindrical parts (3), (5), and (7) inside it; are then fitted into telescoping cylindrical parts (10). When both sides of the devise are assembled as described then telescoping cylindrical parts (3) of each pair should be attached to the electromagnet housing (2).

Actuator components can then be secured into long chains by means of threads (8a), (8b), (11a), and (11b).

Figure 3:
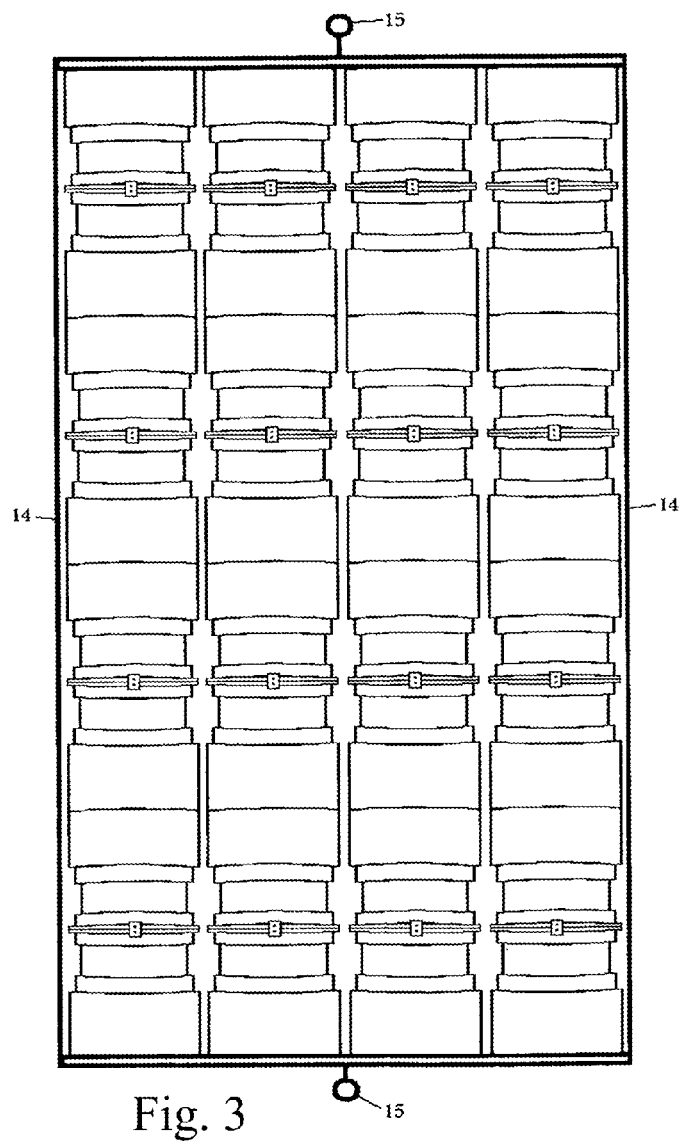
FIG. 3 is a view of an artificial muscle apparatus

Chains of actuators (FIG. 2) should be bundled together to create an artificial muscle apparatus (FIG. 3). The strength of contraction of these bundles is dependent upon the amplitude of current supplied to each actuator, the number of actuators in a chain, and the number of chains in the bundle which are activated. Duration of contraction (and length of contraction, depending on the load on the system) is dependent upon the number of control signals received per unit time. Bundles of chains of actuators may be linked together by their ends (8a), (8b), (11a), and (11b); to create a single contractile unit. A unit of this nature should be surrounded by a flexible, biocompatible sheath (14), (shown as a cut-away) to allow for implantation. This sheath should have terminal components (15) that can be affixed to biological structures such as tendons or bones), as well as to the ends of the contractile unit.

Components of this device should be manufactured using standard milling and/or injection molding techniques.

REFERENCE TO SEQUENCE LISTING, A TABLE, OR A COMPUTER PROGRAM LISTING COMPACT DISC APPENDIX

Not Applicable

The invention claimed is:

1. An actuator that generates contractile force comprising:
A central electromagnet acting upon permanent magnets and ferrous components reflected around said central electromagnet;
said permanent magnet components oriented to generate an attractive force between them and said central electromagnet;
said actuator having springs that; in combination with the said central electromagnet, permanent magnets, and ferrous components; that contract said actuator;
said actuator capable of being extended by external forces;
said actuator having a contracted length at least one half of said actuator's extended length;
the contractile power of said actuator capable of being increased by increasing the amplitude of current supplied to the electromagnet.

2. An actuator as in claim 1, wherein said actuator receives signals from a control system.

3. An actuator as in claim 1, wherein said actuator is encased in a biocompatible sheath;
said biocompatible sheath capable of being affixed to the actuator as well as biological structures.

4. An actuator that generates contractile force comprising:
A central electromagnet acting upon permanent magnets and ferrous components reflected around said central electromagnet;
said permanent magnet components oriented to generate an attractive force between them and said central electromagnet;

said actuator having springs that; in combination with the said central electromagnet, permanent magnets, and ferrous components; that contract said actuator;

said actuator capable of being extended by external forces;

said actuator having a contracted length at least one half of said actuator's extended length;

the contractile power of said actuator capable of being increased by increasing the amplitude of current supplied to the electromagnet;

said actuator capable of being joined, end to end, with other similar actuators to form an actuator chain.

5. An actuator as in claim 4, wherein said actuator receives signals from a control system.

6. An actuator as in claim 4, wherein said actuator is encased in a biocompatible sheath;

said biocompatible sheath capable of being affixed to the actuator chain as well as biological structures.

7. An actuator as in claim 4, said actuator actually joined, end to end, with other similar actuators to form said actuator chain.

8. An actuator chain as in claim 7, wherein the force of contraction of said actuator chain increases with the addition of each new actuator to the chain.

9. An actuator chain as in claim 7, wherein said actuator chain receives signals from a control system.

10. An actuator chain as in claim 7 wherein said actuator chain is encased in a biocompatible sheath;

said biocompatible sheath capable of being affixed to the actuator chain as well as biological structures.

11. An actuator chain as in claim 7, wherein separate chains of actuators can be bundled together to form a bundle of actuator chains.

12. A bundle of actuator chains as in claim 11, wherein the force of contraction of said bundle of actuator chains increases with the addition of each new actuator chain to the bundle.

13. A bundle of actuator chains as in claim 11, wherein said bundle of actuator chains receive signals from a control system.

14. A bundle of actuator chains as in claim 11, wherein said bundle of actuator chains is encased in a biocompatible sheath;

said biocompatible sheath capable of being affixed to the actuator bundle as well as biological structures.

* * * * *